United States Patent
Huang et al.

(10) Patent No.: US 9,938,550 B1
(45) Date of Patent: Apr. 10, 2018

(54) ***AUREOBASIDIUM PULLULANS*, CULTURING MEDIUM AND METHOD FOR PRODUCING β-GLUCAN, A CULTURE OF *AUREOBASIDIUM PULLULANS* AND A COMPOSITION COMPRISING THE SAME**

(71) Applicant: FOOD INDUSTRY RESEARCH AND DEVELOPMENT INSTITUTE, Hsinchu (TW)

(72) Inventors: Chiao-Ying Huang, Hsinchu (TW); Yu-Chen Cheng, Hsinchu (TW); Yi-Sheng Lin, Hsinchu (TW); Guey-Yuh Liou, Hsinchu (TW); Shie-Jea Lin, Hsinchu (TW); Jinn-Tsyy Lai, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 0 days.

(21) Appl. No.: 15/586,381

(22) Filed: May 4, 2017

(30) Foreign Application Priority Data

Nov. 30, 2016 (TW) .............................. 105139432 A

(51) Int. Cl.
*C12N 1/14* (2006.01)
*C12P 19/04* (2006.01)

(52) U.S. Cl.
CPC ................ *C12P 19/04* (2013.01); *C12N 1/14* (2013.01)

(58) Field of Classification Search
CPC ........ A61K 31/70; A61K 31/716; C12N 1/14; C12P 19/04
See application file for complete search history.

(56) References Cited

U.S. PATENT DOCUMENTS 5,789,579 A * 8/1998 Fujii ...................... C12P 19/04
435/101

FOREIGN PATENT DOCUMENTS

| JP | 08157377 | * | 6/1996 |
|----|----------|---|--------|
| JP | 2007267720 A | | 10/2007 |
| JP | 2007319150 A | | 12/2007 |

* cited by examiner

*Primary Examiner* — Maryam Monshipouri
(74) *Attorney, Agent, or Firm* — Haverstock & Owens LLP

(57) ABSTRACT

The present application provides a culture medium for producing β-glucan. The culture medium comprises: a carbon source, a nitrogen source and an ascorbic acid. The present application further provides a method for producing β-glucan, the method comprising culturing *Aureobasidium pullulans* in the culture medium for fermentation. The *Aureobasidium pullulans* is advantageous in producing no melanin; as a result, the yield of β-glucan can be increased and the waste can be reduced with the improved culture medium composition and culturing method.

16 Claims, 12 Drawing Sheets

AUREOBASIDIUM PULLULANS, CULTURING MEDIUM AND METHOD FOR PRODUCING β-GLUCAN, A CULTURE OF AUREOBASIDIUM PULLULANS AND A COMPOSITION COMPRISING THE SAME

BACKGROUND

Technical Field

The present application relates to a method for producing β-glucan, and particularly relates to a method for producing β-glucan with high yields via *Aureobasidium pullulans* generating no melanin and a fermentation culture medium.

Description of Related Art

*Aureobasidium pullulans* is a fungus being similar to yeast. There are polysaccharides, such as β-glucan, around the periphery of the cell wall of the *Aureobasidium pullulans*.

β-glucan is one of the food-grade feedstocks approved publicly by the Taiwan Food and Drug Administration and the Japanese Ministry of Health, Labour and Welfare, as well as a GRAS (Generally Recognized As Safe) food additive approved publicly by the U.S. Food and Drug Administration. There would thus be less food safety concerns when developing β-glucan.

During the extraction process of active ingredients, e.g. β-glucan, from sources such as barley, oat, yeast fungi and mushrooms, a variety of chemical treatments must be applied. Many beneficial trace ingredients may be lost during the process so that expected effects of the product may not be achieved. In addition, the concentration of β-glucan generated from plants may be varied depending on whether the plants are wild or cultivated, or on the conditions and the environment in which they grow. Compared with the generating process using barley, oat, yeast fungi and mushrooms as sources, generating β-glucan from *Aureobasidium pullulans* allows us to skip the extraction step and reduce the generation of liquid waste since β-glucan would be excreted into extracellular culture medium. Furthermore, generating β-glucan from *Aureobasidium pullulans* does not have the same drawbacks as generating β-glucan from the abovementioned plants.

Although generating β-glucan from *Aureobasidium pullulans* may have the beneficial effects mentioned above, there are some limitations:

(1) Low yield: In the fermentation process, *Aureobasidium pullulans* may generate soluble extracellular polysaccharide. However, as the yield of the polysaccharide increases, the fermentation broth becomes viscous and gelatinous, leading to mass transfer or heat transfer problems related to aeration difficulties, dissolved oxygen and stirring, and thereby decreasing the yield of β-glucan.

(2) Difficulty in removing melanin from polysaccharide: The melanin included in the extracellular polysaccharide normally generated during the fermentation of *Aureobasidium pullulans* makes the product less appealing in appearance. Should the melanin be further removed, obstacles for the manufacturing process would increase and may affect subsequent processes for mass production.

SUMMARY

In light of the above problems in the prior art, an object of the present invention is to provide an *Aureobasidium pullulans* that provides β-glucan with higher yields and substantially without melanin.

In one aspect, described herein is an *Aureobasidium pullulans* deposited at National Institute of Technology and Evaluation (NITE), NITE Patent Microorganisms Depositary (NPMD) on Oct. 19, 2016 under the accession number NITE BP-02372.

In another aspect, described herein is a fermentation culture medium for producing β-glucan, comprising: a carbon source, a nitrogen source and an ascorbic acid; wherein the carbon source is selected from a group consisting of: lactose, fructose, maltose, glucose, galactose, xylose, xylitol, inulin, sorbitol, fucose, sucrose, molasses and a combination thereof; and wherein the nitrogen source is selected from a group consisting of: peptone from soybean (enzymatic digest), yeast extract granulated, urea, potassium nitrate, sodium nitrate, ammonium sulfate, lecithin and a combination thereof.

Preferably, the carbon source may be sucrose or glucose. Preferably, a concentration of the sucrose may be 10-70 g/L based on a total volume of the culture medium. Preferably, a concentration of the glucose may be 25-150 g/L based on a total volume of the culture medium.

Preferably, the nitrogen source may be lecithin. Preferably, a concentration of the lecithin may be lower than or equal to 6 g/L based on a total volume of the culture medium. Preferably, a concentration of the ascorbic acid may be lower than or equal to 6 g/L based on a total volume of the culture medium.

Preferably, an initial pH value of the fermentation culture medium may be 4-8. Preferably, an initial pH value of the fermentation culture medium may be 5-6.

In one aspect, described herein is a fermentation culture medium for producing β-glucan, comprising: a carbon source and an ascorbic acid; wherein the carbon source is selected from a group consisting of: lactose, fructose, maltose, glucose, galactose, xylose, xylitol, inulin, sorbitol, fucose, sucrose, molasses and a combination thereof; and wherein the fermentation culture medium may comprise no nitrogen source.

In one aspect, described herein is a method for producing β-glucan, comprising: culturing the *Aureobasidium pullulans* in a fermentation culture medium to ferment the *Aureobasidium pullulans*.

Preferably, the fermentation culture medium may be the culture medium described above.

Preferably, the *Aureobasidium pullulans* may be cultured at 15-30° C.

Preferably, the fermentation may be carried out with a rotation speed of 150-350 rpm.

Preferably, the fermentation may be carried out with a ventilation of 1-2 vvm.

Preferably, the method may further comprise culturing the *Aureobasidium pullulans* in an inoculum culture medium to enable the *Aureobasidium pullulans* to proliferate until a stationary phase before fermentation.

Preferably, the inoculum culture medium may comprise yeast extract granulated, malt extract, peptone from soybean (enzymatic digest), dextrose and $H_2O$.

In one aspect, described herein is an *Aureobasidium pullulans* culture comprising β-glucan and may be produced by the method described above.

In one aspect, described herein is a composition comprising the *Aureobasidium pullulans* culture described above, and an optional carrier.

In general, the present invention at least provides the following advantages:

(1) According to one embodiment of the present invention, the *Aureobasidium pullulans* does not produce melanin so that melanin removal after extraction can be skipped. In addition, by improving the fermentation culture medium and the culturing method, the yield of β-glucan can be effectively increased.

(2) By improving the fermentation culture medium and the manufacturing process of β-glucan, all the fermentation broth of the *Aureobasidium pullulans* can be used to manufacture a product having a high content of β-glucan. Apart from its improved efficacy, the product can be easily stored and further processed. Liquid waste generated by the manufacturing process can therefore be reduced at the same time to achieve the goal of conserving energy and being environment-friendly.

These and other objects features and advantages of the present invention will become more apparent from the following detailed description, appended claims and accompanying drawings.

Figure 1:
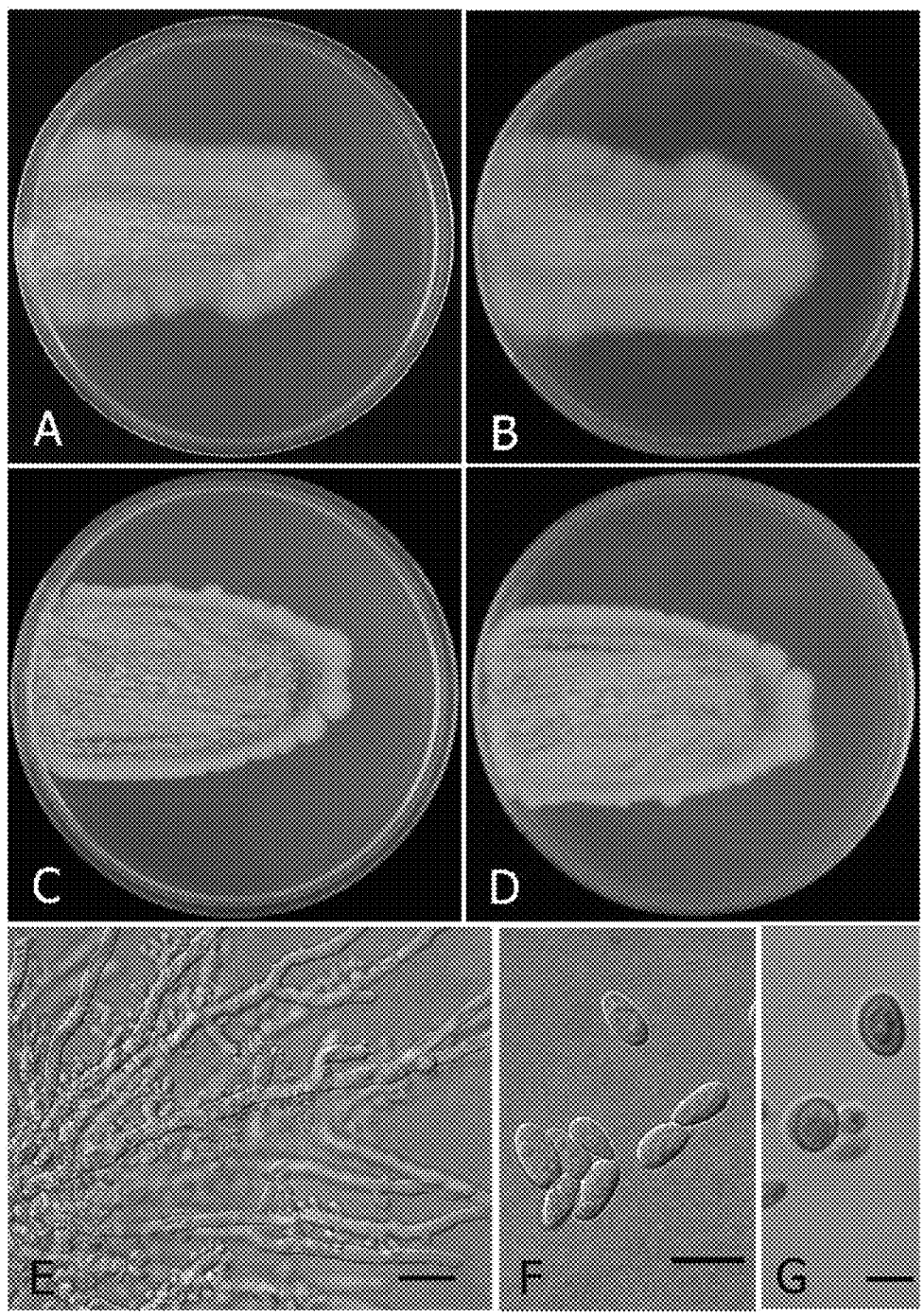
FIG. 1 shows morphology features and microscopic structures of *Aureobasidium pullulans* 12F0291: (A) a front view of a colony after 5 days on MEA at 25° C.; (B) a back view of a colony after 5 days on MEA at 25° C.; (C) a front view of a colony after 5 days on PDA at 25° C.; (D) a back view of a colony after 5 days on PDA at 25° C.; (E) features of hyphae and conidiogenous cells (bar=10 μm); (F) conidia (bar=10 μm); (G) chlamydospores (bar=5 μm).

Concrete details are given in the following detailed description as illustrations of the present invention, in order to provide a thorough understanding of the disclosed embodiments. It is obvious, however, that one or more embodiments can be implemented without the described concrete details. In other cases, structures and procedures of prior art will be shown in illustrative displays to simplify the accompanying drawings.

DETAILED DESCRIPTION

Detailed description of each embodiment of the present invention will be provided hereinafter. Other features of the present invention will be clearly shown with this description and the claims.

It is to be understood, without further explanation, that a person of ordinary skill in the art can make use of the present invention to the greatest extent based on this description. This description is not to be taken in a limiting sense, but is made merely for the purpose of illustrating the general principles of the invention.

Unless otherwise described, all technical and scientific terms used hereinafter are understood in the same way a person of ordinary skill in the art understands them.

The article "a" hereinafter refers to one or more (i.e. at least one) objects, in grammatical terms, of the article.

Selection of *Aureobasidium pullulans* Strains with Potential

Primary Screening:

The *Aureobasidium pullulans* kept in frozen stock tubes were thawed and spread over on a culture medium used for primary screening (ingredients shown in Table 1). The strains were cultured for 5 to 7 days at 25° C., and those having undergone obvious color change were selected. Of the 530 strains in the primary screening, 30 strains with potential were shortlisted for subsequent selections.

TABLE 1

| Culture medium used for primary screening (YM agar + Sucrose + Aniline blue) | |
|---|---|
| Ingredient | Concentration (g/L) |
| Yeast extract | 3 |
| Malt extract | 3 |
| Peptone | 5 |
| Dextrose | 10 |
| Sucrose | 20 |
| Aniline blue | 0.05 |
| Agar | 15 | pH 6.2 ± 0.2

Selection from Shortlisted Strains

From the 30 strains shortlisted during the primary screening, potentially productive strains were further screened and selected for a production test. Briefly, this selection procedure is as follows: first, shortlisted strains were thawed and grown on a YMS medium with sucrose (ingredients shown in Table 2) for 4 days at 25° C. using shake culture technique; secondly, pullulanase was used to decompose pullulan after samples had been gathered from the medium; and finally, total carbohydrates of each strain were measured using phenol-sulfuric acid assay to select strains with higher yields of non-pullulan polysaccharides.

TABLE 2

| YMS medium (YM broth + Sucrose) | |
|---|---|
| Ingredient | Concentration (g/L) |
| Yeast extract | 3 |
| Malt extract | 3 |

TABLE 2-continued

YMS medium (YM broth + Sucrose)

| Ingredient | Concentration (g/L) |
|---|---|
| Peptone | 5 |
| Dextrose | 10 |
| Sucrose | 20 | pH 6.2 ± 0.2

The selected *Aureobasidium pullulans* strains with potential of producing β-glucan were then revived in a YM medium (Difco™) and kept in a YMS medium in a shake flask to culture for 72 hours at 25° C. with an rotation speed of 150 rpm. After the culture, β-glucan in a fermentation broth in the shake flask was measured. The method of measurement is described hereafter and the results are shown in Table 3, wherein LQ is a fermentation broth of *Aureobasidium pullulans* with a β-glucan concentration of 1% (10 g/L), which was purchased from ADEKA, Japan, and used as a positive control.

Method for Measuring β-Glucan in *Aureobasidium pullulans*

A Total Dietary Fiber Assay kit (Megazyme) was used as for β-glucan measurement. First, a portion of the fermentation broth was evenly mixed with an appropriate volume of buffer solution. Secondly, three enzymes were added into the resulting mixture in the following order: α-amylase, protease, and amyloglucosidase. A volume of alcohol four times the volume of the resulting mixture was then added to precipitate β-glucan. A precipitate was collected, washed with alcohol and dried to be hydrolyzed with a strong acid at a high temperature. After acid-base neutralization, a concentration of β-glucan was measured. Detailed descriptions about the above steps are as follows:

When a sample was a fermentation broth, 5 grams of the sample was added into 3.5 mL 0.08M phosphate-buffered solution (pH 6.0) to be evenly mixed.

500 μL α-amylase (60 mg/mL in PB buffer) was added into the sample. The resulting solution was heated for 30 minutes in a water bath at 95° C. and shaken every 15 minutes to obtain an even mixture. The sample was cooled down to 60° C. and was adjusted with 0.275 M NaOH to a pH of 7.5±0.1 (about 1000 μL). 50 μL of protease was then added to the sample, and the solution was heated for 30 minutes in a water bath at 60° C., and adjusted with 0.325 M HCl to a pH of 4.3±0.1 (about 800 μL). 50 μL of amyloglucosidase was finally added and the resulting mixture was heated for 30 minutes in a water bath at 60° C. to obtain an enzyme-processed sample.

The enzyme-processed sample was made up to 40 mL with 95% EtOH. The resulting mixture was left standing for an hour at room temperature to precipitate β-glucan from the solution. The precipitate was centrifuged at 10,000 g for 10 minutes to remove a supernatant. After collection, the precipitate was washed with 4 mL 80% EtOH, centrifuged for 5 minutes to remove a supernatant, and then dried in a vacuum deaerator at room temperature.

1 mL 72% (w/v) sulfuric acid was added to the sample dried overnight. The resulting mixture was left standing for 60 minutes at room temperature, and 14 mL deionized water was then added into the mixture. The resulting solution was heated for 2 hours in a boiling water bath (100° C.). When large residue pieces were still present, the solution was further sterilized with Autoclave (121° C., 20 minutes). The hydrolysate solution was cooled down, neutralized with 5 mL 5 N NaOH, and made up to a volume of 25 mL with deionized water. A concentration of glucose of the solution was then measured using a glucose PAP kit.

During the above procedures, polysaccharides having alpha-glycosidic linkages in the fermentation broths were decomposed by α-amylase, macromolecules of proteins in the fermentation broths were decomposed by protease, and short-chain glucose polymers were broken down into glucose by amyloglucosidase. Long-chain glucose polymers that were not decomposed by the above enzymes (only glucose polymers with beta-glycosidic linkages remained) were precipitated by alcohol from the solution to be dried. Once the precipitate was dried, a concentration of glucose was measured using sulfuric acid for hydrolysis at a high temperature to obtain a concentration of glucose polymers with beta-glycosidic linkages. A weight of the glucose polymers ($W_{BGP}$) was calculated according to the following formula and the concentration of glucose ($C_{glu}$) obtained through this enzymatic method:

$$W_{BGP} = C_{glu} \times 0.9 \times 1000 \times 0.025$$

where 0.025 is a dilution factor (25 mL/1 L); and
where 1000 is a unit factor (mg/g).

TABLE 3

Measurements of β-glucan in *Aureobasidium pullulans* strains with potential cultured primarily for 3 days in shake flasks

| Strain No. | $OD_{505nm}$ | $\Delta OD_{505nm}$ | Average $\Delta OD_{505nm}$ | Glucose concentration (g/L) | β-glucan concentration (g/L) |
|---|---|---|---|---|---|
| 1 | 0.078 | 0.017 | 0.019 | 0.06 | 1.35 |
| 2 | 0.083 | 0.022 | 0.021 | 0.07 | 1.53 |
| 3 | 0.083 | 0.022 | 0.022 | 0.07 | 1.60 |
| 4 | 0.082 | 0.021 | 0.021 | 0.07 | 1.53 |
| 5 | 0.092 | 0.031 | 0.031 | 0.10 | 2.26 |
| 6 | 0.091 | 0.030 | 0.032 | 0.10 | 2.33 |
| LQ | 0.188 | 0.127 | 0.124 | 0.40 | 9.03 |

In view of the measurements of β-glucan concentration in Table 3, strain 6 was selected as the best strain with potential, and was named *Aureobasidium pullulans* 12F0291.

Strain Identification

According to one embodiment of the invention, *Aureobasidium pullulans* 12F0291 with potential of producing β-glucan and selected from a species pool of *Aureobasidium pullulans* at Food Industry Research and Development Institute is deposited at National Institute of Technology and Evaluation (NITE), NITE Patent Microorganisms Depositary (NPMD) on Oct. 19, 2016 under the accession number NITE BP-02372.

*Aureobasidium pullulans* 12F0291 was isolated on Jun. 17, 2008 from plant leaves found in Xinpu in Hsinchu County, Taiwan. As shown in FIG. 1, (A) and (B), *Aureobasidium pullulans* 12F0291 was spread on an Malt Extract Agar (MEA, Blakeslee's Formula) as described in Table 4, and cultured at 25° C. Colonies formed on the agar appeared smooth and viscous with clear and sticky mucus on the surface. The color of the colonies changed from yellow-gray to orange-brown, while periphery of the colonies appeared yellow-white. As shown in FIG. 1, (C) and (D), *Aureobasidium pullulans* 12F0291 was spread on a Potato Dextrose Agar (PDA, Difco™) as described in Table 5, and cultured at 25° C. Colonies formed on the medium appeared smooth and viscous with clear and sticky mucus on the surface. The color of the colonies changed from yellow-white to orange-red, while periphery of the colonies appeared yellow-white.

TABLE 4

MEA (Blakeslee's Formula)

| Ingredient | Concentration (g/L) |
| --- | --- |
| Malt extract | 20 |
| Glucose | 20 |
| Peptone | 1 |
| Agar | 20 |

TABLE 5

PDA (Difco ™)

| Ingredient | Concentration (g/L) |
| --- | --- |
| Potato starch | 4 |
| Dextrose | 20 |
| Agar | 15 |

As shown in FIG. 1, (E) to (G), strains of *Aureobasidium pullulans* 12F0291 under a microscope appeared smooth with visible transverse septa, and slightly narrowed near the transverse septa, with thin wall to thick wall ranging from 3.4 to 5.8 µm in diameter. A part of strains gradually turned orange-brown as the culture process continued. Conidiogenous cells were undifferentiated and grew from the middle or the end of a colorless hyphae, only sometimes from a strain branch. Also, these cells had denticles from which conidia were produced. An external wall of the conidia appeared smooth in diverse forms, and was 4.0-11.0×3.0-6.0 µm in size. Chlamydospores were colorless or orange-brown in color, quasi spherical or oval in shape, and 4.7-9.0×2.9-6.5 µm in size.

ITS1-5.8S-ITS2 segments of an rDNA of *Aureobasidium pullulans* 12F0291 were sequenced and compared. Results showed that *Aureobasidium pullulans* 12F0291 shared most traits with *Aureobasidium pullulans* var. *melanogenum* BCRC 34543T (=CBS 105.22T, BCRC database no. BCRC34543_05042009_FD_ITS) and *Aureobasidium pullulans* NRRL Y-12996 (=ATCC 42023, GenBank accession no. HQ702508).

With the features of the above colonies, conidiogenous cells and conidia, as well as the sequencing results of ITTS-5.8S-ITSS2 of the rDNA, *Aureobasidium pullulans* 12F0291 was identified as belonging to *Aureobasidium pullulans* and as *Aureobasidium pullulans* var. *melanogenum*.

A Fermentation Culture Medium for Producing β-Glucan

In view of the above problems, one embodiment of the invention relates to a culture medium used for producing β-glucan. The culture medium might comprise: a carbon source, a nitrogen source and an ascorbic acid, wherein the carbon source might be selected from a group consisting of: lactose, fructose, maltose, glucose, galactose, xylose, xylitol, inulin, sorbitol, fucose, sucrose, molasses and a combination thereof, and wherein the nitrogen source might be selected from a group consisting of: peptone from soybean (enzymatic digest), yeast extract granulated, urea, potassium nitrate, sodium nitrate, ammonium sulfate, lecithin and a combination thereof.

In a preferred embodiment, the carbon source might be sucrose or glucose. In a more preferred embodiment, the sucrose might have a concentration of 10-70 g/L, or the glucose might have a concentration of 25-150 g/L, based on a total volume of the culture medium. In another preferred embodiment, the nitrogen source might be lecithin, and a concentration of the lecithin might be lower than or equal to 6 g/L.

According to one embodiment of the invention, the culture medium used for producing β-glucan could be prepared with the following procedure. Ascorbic acid was added when preparing a culture medium, with a pH being about 3.0. The pH was then adjusted with $NaOH_{(aq)}$ to from 4.0 to 8.0, preferably from 5.0 to 6.0. The medium was then sterilized using an autoclave, and inoculated after being cooled. In another embodiment, a pH might be adjusted to 12.0 when preparing a culture medium. When the medium was sterilized in an autoclave, a solution of ascorbic acid was filtered through a 0.22 µm filter in a laminar flow cabinet, and then added into the sterilized medium, thereby allowing the medium to have a pH of 4.0 to 8.0, preferably 5.0 to 6.0, before inoculation. In a more preferred embodiment, a concentration of the ascorbic acid might be lower than or equal to 6 g/L.

According to one embodiment of the invention, *Aureobasidium pullulans* 12F0291 frozen in a glycerol stock was thawed and revived, and 0.3% (v/v) of the *Aureobasidium pullulans* was inoculated in a YM medium (ingredients shown in Table 6) and cultured for 48 hours at 25° C. with a rotation speed of 150 rpm. The resulting culture was inoculated into the following fermentation culture media (Table 7 to Table 13) and grown for 2 days at 25° C. with a rotation speed of 150 rpm. A concentration of β-glucan in each fermentation culture medium was measured using the aforementioned method of measurement that will not be further explained here.

TABLE 6

YM broth (Difco ™)

| Ingredient | Concentration (g/L) |
| --- | --- |
| Yeast extract | 3 |
| Malt extract | 3 |
| Peptone | 5 |
| Dextrose | 10 | pH 6.2 ± 0.2

Figure 2:
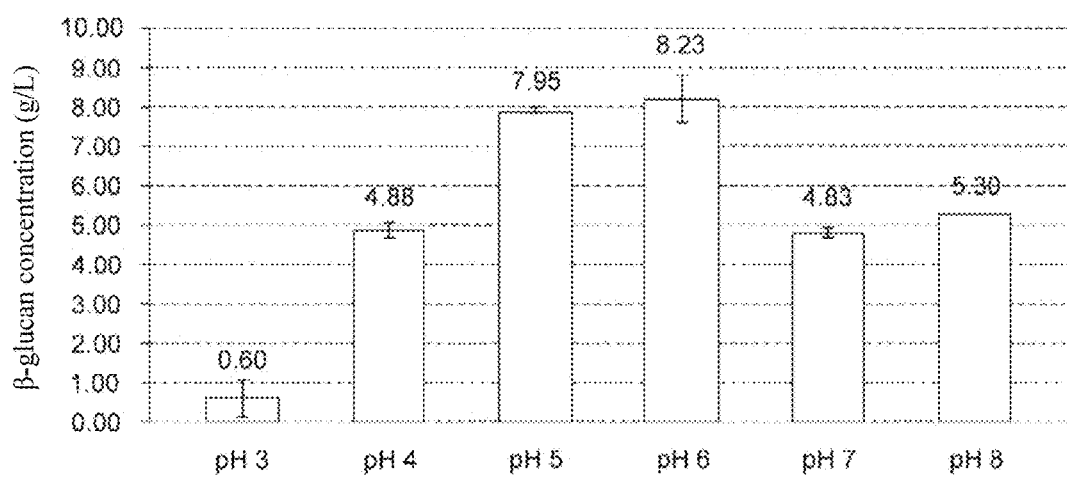
FIG. 2 illustrates concentration test results of β-glucan produced in fermentation culture media with various initial pH values.

In one embodiment, *Aureobasidium pullulans* 12F0291 was inoculated into SCL fermentation culture media at an initial pH of 3.0, 4.0, 5.0, 6.0, 7.0 and 8.0, respectively, and left to ferment and produce β-glucan. A concentration of β-glucan produced during fermentation on each medium was measured. The "initial pH" used herein refers to a pH value of a culture medium which was prepared and yet to be inoculated. Results shown in FIG. 2 were gathered from a concentration measurement of β-glucan produced on fermentation culture media of various initial pH. As shown in FIG. 2, in fermentation culture media at a pH from 4.0 to 8.0, *Aureobasidium pullulans* 12F0291 was able to produce more β-glucan. In media at pH 5.0 and 6.0 in particular, *Aureobasidium pullulans* 12F0291 produced the most β-glucan with a concentration of 7.95 g/L and 8.23 g/L, respectively.

Figure 3:
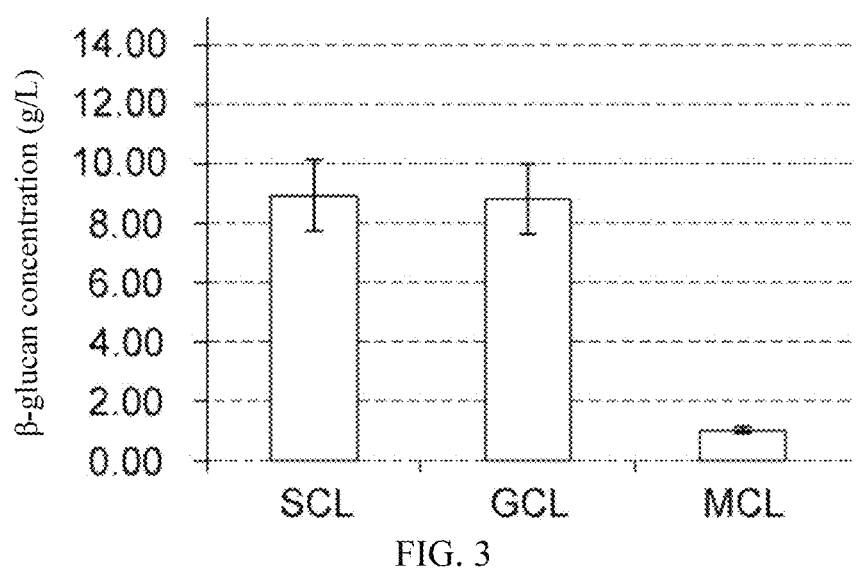
FIG. 3 illustrates concentration test results of β-glucan produced in fermentation culture media with various carbon sources.

In one embodiment, *Aureobasidium pullulans* 12F0291 was inoculated and left to ferment in fermentation culture media containing various carbon sources. In this embodiment specifically, *Aureobasidium pullulans* were inoculated into fermentation culture media which used sucrose (SCL, ingredients shown in Table 7), glucose (GCL, ingredients shown in Table 8) or molasses (MCL, ingredients shown in Table 9) as a carbon source, respectively. A concentration of β-glucan produced in each medium during fermentation was measured. Results shown in FIG. 3 were gathered from a concentration measurement of β-glucan produced in fermentation culture media containing various carbon sources. As shown in FIG. 3, in a fermentation culture medium where SCL, GCL or MCL was used as a carbon source, *Aureobasidium pullulans* 12F0291 was able to produce β-glucan. In SCL and GCL media in particular, *Aureobasidium pullulans* 12F0291 produced the most β-glucan with a concentration of about 9 g/L.

TABLE 7

SCL fermentation culture medium

| Ingredient | Concentration (g/L) |
|---|---|
| Sucrose | 50 |
| Ascorbic acid | 4 |
| Lecithin | 2 | pH 5.55

TABLE 8

GCL fermentation culture medium

| Ingredient | Concentration (g/L) |
|---|---|
| Glucose | 50 |
| Ascorbic acid | 4 |
| Lecithin | 2 | pH 5.51

TABLE 9

MCL fermentation culture medium

| Ingredient | Concentration (g/L) |
|---|---|
| Molasses | 50 |
| Ascorbic acid | 4 |
| Lecithin | 2 | pH 5.54

Figure 4:
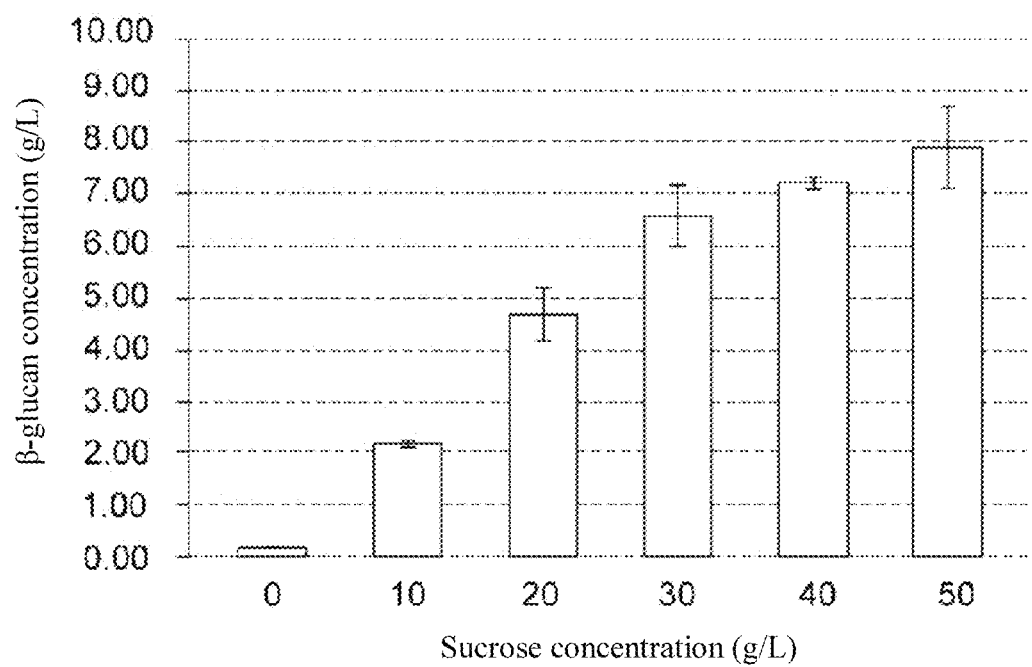
FIG. 4 illustrates concentration test results of β-glucan produced in fermentation culture media with sucrose in various concentrations.

In a preferred embodiment, *Aureobasidium pullulans* 12F0291 were inoculated into fermentation culture media with various concentrations of sucrose, and left to ferment and produce β-glucan. In this embodiment specifically, *Aureobasidium pullulans* 12F0291 were inoculated into fermentation culture media with a sucrose concentration of 0, 10, 20, 30, 40, and 50 g/L (ingredients shown in Table 10), respectively. A concentration of β-glucan produced on each medium during fermentation was measured. Results shown in FIG. 4 were gathered from a concentration measurement of β-glucan produced on fermentation culture media with various concentrations of sucrose. As shown in FIG. 4, a concentration of β-glucan produced during fermentation increases with an increasing concentration of sucrose in a culture medium. In this embodiment, *Aureobasidium pullulans* 12F0291 in the culture medium with 50 g/L of sucrose produced β-glucan with the highest concentration of about 8 g/L.

TABLE 10

Fermentation culture media with various concentrations of sucrose

| Ingredient | Concentration (g/L) |
|---|---|
| Sucrose | 0, 10, 20, 30, 40, 50 |
| Ascorbic acid | 4 |
| Lecithin | 4 |
| Bran | 4 | pH 5.55-5.60

Figure 5:
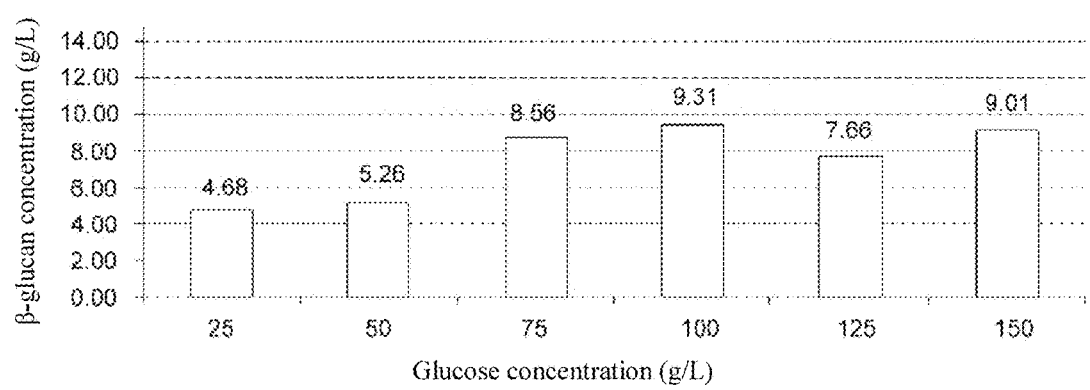
FIG. 5 illustrates concentration test results of β-glucan produced in fermentation culture media with glucose in various concentrations.

In a preferred embodiment, *Aureobasidium pullulans* 12F0291 were inoculated onto fermentation culture media with various concentrations of glucose, and left to ferment and produce β-glucan. In this embodiment specifically, *Aureobasidium pullulans* 12F0291 were inoculated onto fermentation culture media with a glucose concentration of 25, 50, 75, 100, 125, and 150 g/L (ingredients shown in Table 11), respectively. A concentration of β-glucan produced on each medium during fermentation was measured. Results shown in FIG. 5 were gathered from a concentration measurement of β-glucan produced on fermentation culture media with various concentrations of glucose. As shown in FIG. 5, a concentration of β-glucan produced during fermentation increases roughly with an increasing concentration of glucose in a culture medium. In this embodiment, *Aureobasidium pullulans* 12F0291 in the culture medium with 100 g/L of glucose produced β-glucan with the highest concentration of about 9.31 g/L.

TABLE 11

Fermentation culture media with various concentrations of glucose

| Ingredient | Concentration (g/L) |
|---|---|
| Glucose | 25, 50, 75, 100, 125, 150 |
| Ascorbic acid | 4 |
| Lecithin | 2 | pH 5.56-5.62

In one embodiment, the GCL fermentation culture media shown in Table 8 were used as basic culture media, and various nitrogen sources including urea, peptone from soybean (enzymatic digest), yeast extract granulated, $KNO_3$, $NaNO_3$ and $(NH_4)_2SO_4$ were further added to each medium respectively. In one embodiment, a concentration of the nitrogen source added might be 2, 4 or 8 g/L. An initial pH of each one of the culture media with various nitrogen sources was adjusted to different levels in order shown in Table 12. 20% (v/v) of broth of a YM medium that cultured for 48 hours was inoculated into GCL fermentation culture media containing various nitrogen sources, and cultured in a shake flask for 48 hours at 25° C., with a rotation speed of 150 rpm. A concentration of β-glucan was then measured.

TABLE 12

GCL fermentation culture media containing various nitrogen sources

| Group | Basic culture medium | Nitrogen source | Concentration of nitrogen source (g/L) | Initial pH of culture medium |
|---|---|---|---|---|
| 1 | GCL | N/A | 0 | 5.60 |
| 2 | GCL | Urea | 2, 4, 8 | 5.52, 5.53, 5.60 |
| 3 | GCL | Peptone | 2, 4, 8 | 5.51, 5.53, 5.50 |
| 4 | GCL | Yeast extract | 2, 4, 8 | 5.50, 5.54, 5.46 |

TABLE 12-continued

GCL fermentation culture media containing various nitrogen sources

| Group | Basic culture medium | Nitrogen source | Concentration of nitrogen source (g/L) | Initial pH of culture medium |
|---|---|---|---|---|
| 5 | GCL | KNO$_3$ | 2, 4, 8 | 5.55, 5.52, 5.60 |
| 6 | GCL | NaNO$_3$ | 2, 4, 8 | 5.60, 5.52, 5.60 |
| 7 | GCL | (NH$_4$)$_2$SO$_4$ | 2, 4, 8 | 5.56, 5.57, 5.51 |

Figure 6:
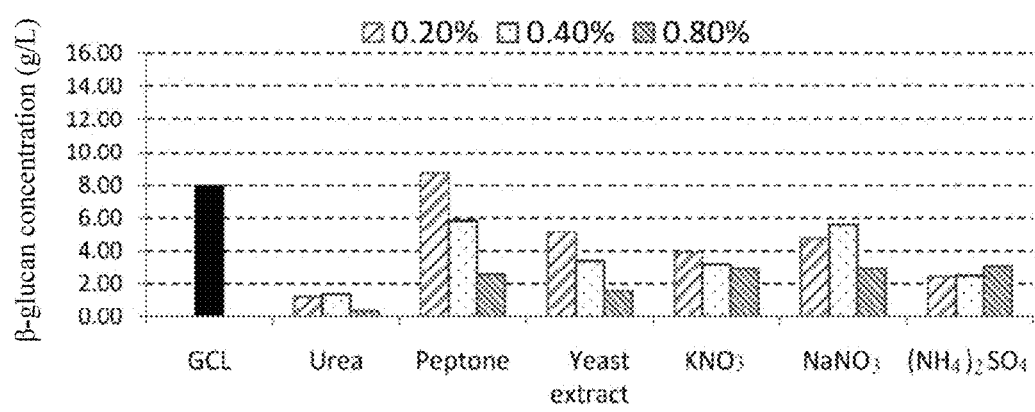
FIG. 6 illustrates concentration test results of β-glucan produced in GCL fermentation culture media with various nitrogen sources.

Results shown in FIG. 6 were gathered from a concentration measurement of β-glucan produced on GCL fermentation culture media containing various nitrogen sources. As shown in FIG. 6, in a fermentation culture medium of any nitrogen source, *Aureobasidium pullulans* 12F0291 fermented and produced β-glucan. It should be noted that in groups where peptone from soybean (enzymatic digest), yeast extract granulated and KNO$_3$ were added (groups 3, 4 and 5), concentrations of β-glucan decreased as concentrations of the added nitrogen sources increased. In groups where urea and NaNO$_3$ were added (groups 2 and 6), each of the groups with 4 g/L nitrogen source produced the most β-glucan, but the increase was not significant comparing to the group with 2 g/L nitrogen source, while the group with 8 g/L nitrogen source produced β-glucan with the lowest concentration. In a group where only lecithin was added (group 1), *Aureobasidium pullulans* 12F0291 produced, after 48 hours of culture, β-glucan with a concentration of 8 g/L, about four times as much as the group where (NH$_4$)$_2$SO$_4$ was added.

Fermentation Culture Medium for Producing β-Glucan without a Nitrogen Source

In this embodiment, *Aureobasidium pullulans* 12F0291 were inoculated and left to ferment and produce β-glucan in fermentation culture media without any nitrogen sources. In this embodiment specifically, *Aureobasidium pullulans* 12F0291 were inoculated and left fermented on fermentation culture media used for producing β-glucan. The culture medium comprised a carbon source and an ascorbic acid, wherein the carbon source might be selected from a group consisting of: lactose, fructose, maltose, glucose, galactose, xylose, xylitol, inulin, sorbitol, fucose, sucrose and a combination thereof, and wherein the culture medium might contain no nitrogen sources.

Figure 7:
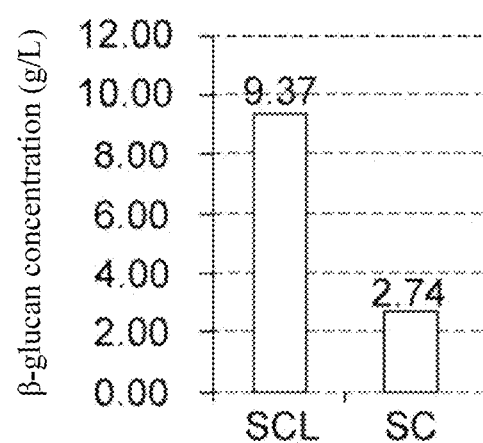
FIG. 7 illustrates concentration test results of the *Aureobasidium pullulans* produced in fermentation culture media with or without nitrogen sources.

In one embodiment, lecithin was used as a nitrogen source for fermentation of *Aureobasidium pullulans* 12F0291. In other words, *Aureobasidium pullulans* 12F0291 was inoculated and left to ferment in the fermentation culture media containing lecithin (such as the SCL fermentation culture medium shown in Table 7) as a nitrogen source or in other fermentation culture media containing no nitrogen sources (like the ingredients of SC fermentation culture medium shown in Table 13). A concentration of β-glucan after fermentation was measured. Results in FIG. 7 were gathered from concentration measurements of β-glucan produced by *Aureobasidium pullulans* 12F0291 grown on fermentation culture media containing or not containing nitrogen sources. As shown in FIG. 7, in both fermentation culture media containing and not containing lecithin, *Aureobasidium pullulans* 12F0291 were able to produce β-glucan. Nevertheless, *Aureobasidium pullulans* 12F0291 grown in the culture medium containing lecithin produced more β-glucan with a concentration of about 9.37 g/L, while *Aureobasidium pullulans* 12F0291 grown on the culture medium not containing lecithin produced β-glucan with a concentration of about 2.74 g/L.

TABLE 13

SC fermentation culture medium

| Ingredient | Concentration (g/L) |
|---|---|
| Sucrose | 50 |
| Ascorbic acid | 4 |

Manufacturing Process for Producing β-Glucan

This embodiment provides a method for producing β-glucan, and the method includes a fermentation process by culturing the above *Aureobasidium pullulans* in fermentation culture media. In one embodiment, the fermentation culture medium might be any of the aforementioned fermentation culture media, and the culturing process might be carried out under the following conditions:

In one embodiment, *Aureobasidium pullulans* might be cultured at 15-37° C., more preferably at 20-35° C., and most preferably at 23-30° C. In one embodiment, *Aureobasidium pullulans* might be cultured with a rotation speed of 100-450 rpm, preferably with a rotation speed of 120-400 rpm, and most preferably with a rotation speed of 150-350 rpm. In one embodiment, *Aureobasidium pullulans* might be cultured with a ventilation of 0.5-3 vvm, preferably with a ventilation of 0.8-2.5 vvm, and most preferably with a ventilation of 1-2 vvm.

Several specific culture conditions illustrating the method are shown in Table 14. Strains of *Aureobasidium pullulans* were cultured and left to ferment under these conditions. A concentration of β-glucan in post-fermentation broth was measured in each condition. It was found that *Aureobasidium pullulans* was able to produce β-glucan under any of these conditions (not shown in the drawings).

TABLE 14

Different conditions for *Aureobasidium pullulans* fermentation

| Group | Temperature | Amount of ventilation | Rotation speed | Culture period (day) |
|---|---|---|---|---|
| 1 | 15 | 0.5 | 350 | 3 |
| 2 | 15 | 1.5 | 200 | 4 |
| 3 | 18 | 2 | 100 | 6 |
| 4 | 20 | 0.8 | 150 | 8 |
| 5 | 23 | 2.5 | 450 | 3 |
| 6 | 20 | 3 | 250 | 4 |
| 7 | 25 | 1 | 200 | 6 |
| 8 | 25 | 1.5 | 120 | 8 |
| 9 | 37 | 3 | 300 | 3 |

Figure 8:
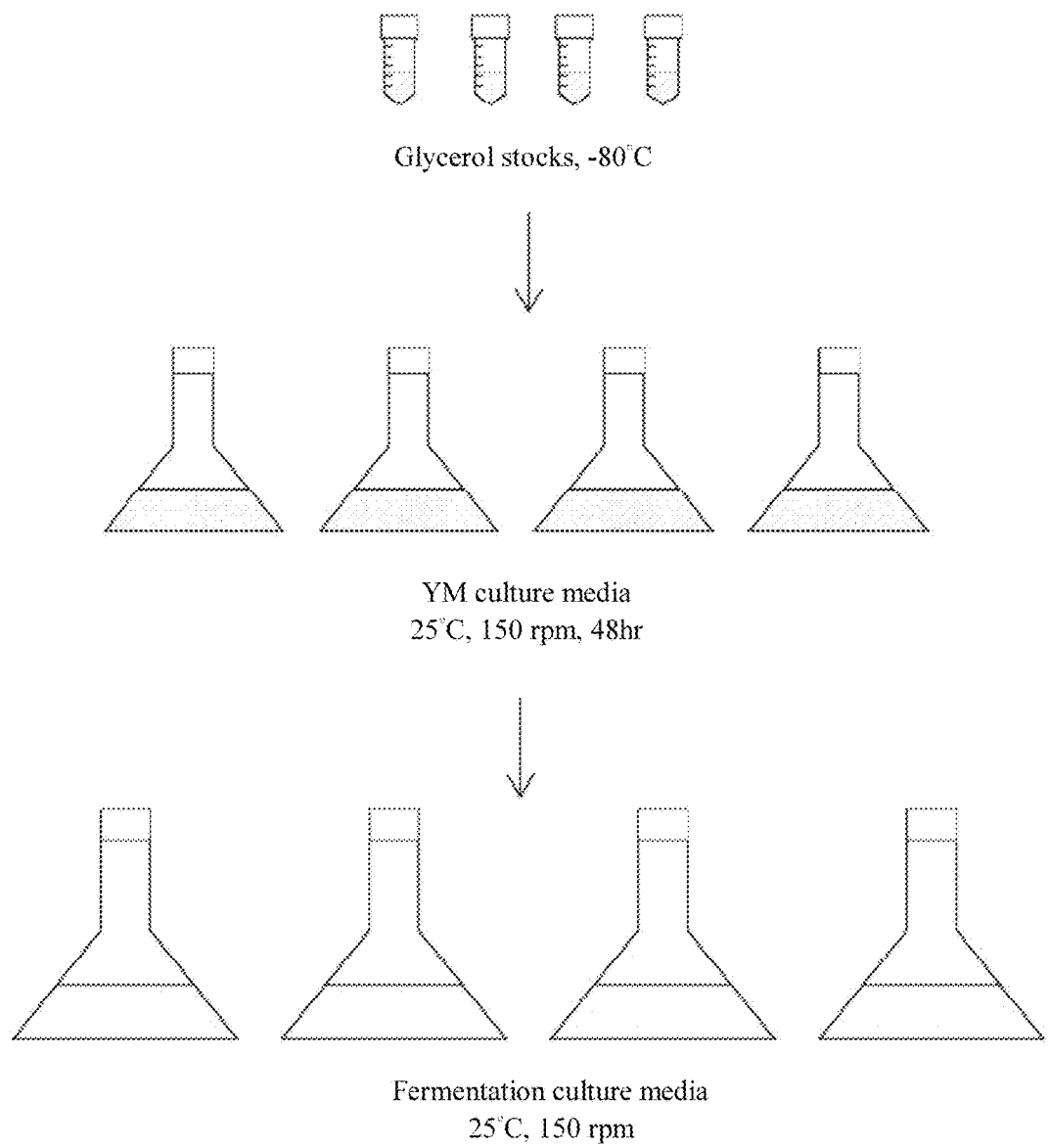
FIG. 8 is a schematic view showing a procedure of thawing the *Aureobasidium pullulans* frozen in glycerol stocks, followed by cell culture and fermentation.

To be more specific, please refer to FIGS. 8 to 12. FIG. 8 illustrates a procedure of thawing, culturing and fermenting *Aureobasidium pullulans* 12F0291 and strains 3, 4, and 5 (i.e., strains with potential) shown in Table 3, all of which were initially stored in glycerol stocks. Each of the above *Aureobasidium pullulans* strains was thawed and inoculated with an inoculum quantity of 0.3% from a glycerol stock into an YM medium shown in Table 6, and cultured in a shake flask for 48 hours at 25° C. with a rotation speed of 150 rpm. The broths after culture were re-inoculated into High-GCL fermentation culture media shown in Table 15, and cultured at 25° C. with a rotation speed of 150 rpm for 2, 5, 6 and 8 days, respectively, to produce β-glucan. In a preferred embodiment, each *Aureobasidium pullulans* strain was cultured in an YM culture medium, thereby allowing the *Aureobasidium pullulans* to proliferate until a stationary phase before fermentation on a fermentation culture medium.

TABLE 15

High-GCL fermentation culture medium

| Ingredient | Concentration (g/L) |
|---|---|
| Glucose | 100 |
| Ascorbic acid | 4 |
| Lecithin | 2 |

Figure 9:
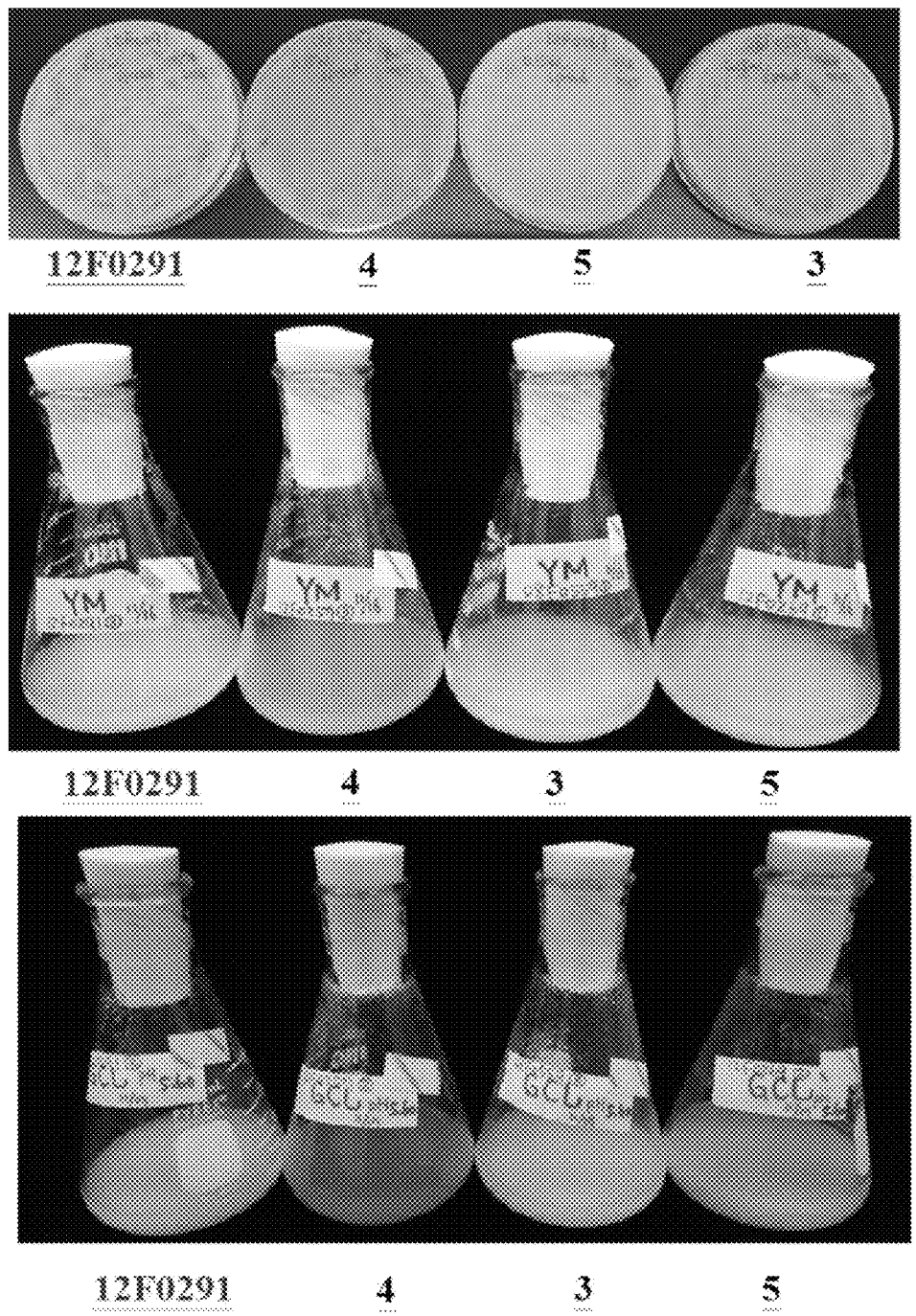
FIG. 9 illustrates colonies of the *Aureobasidium pullulans* cultured on YMA (YM agar) and in a YM medium or fermented in a fermentation culture medium, as well as flasks.
Figure 10:
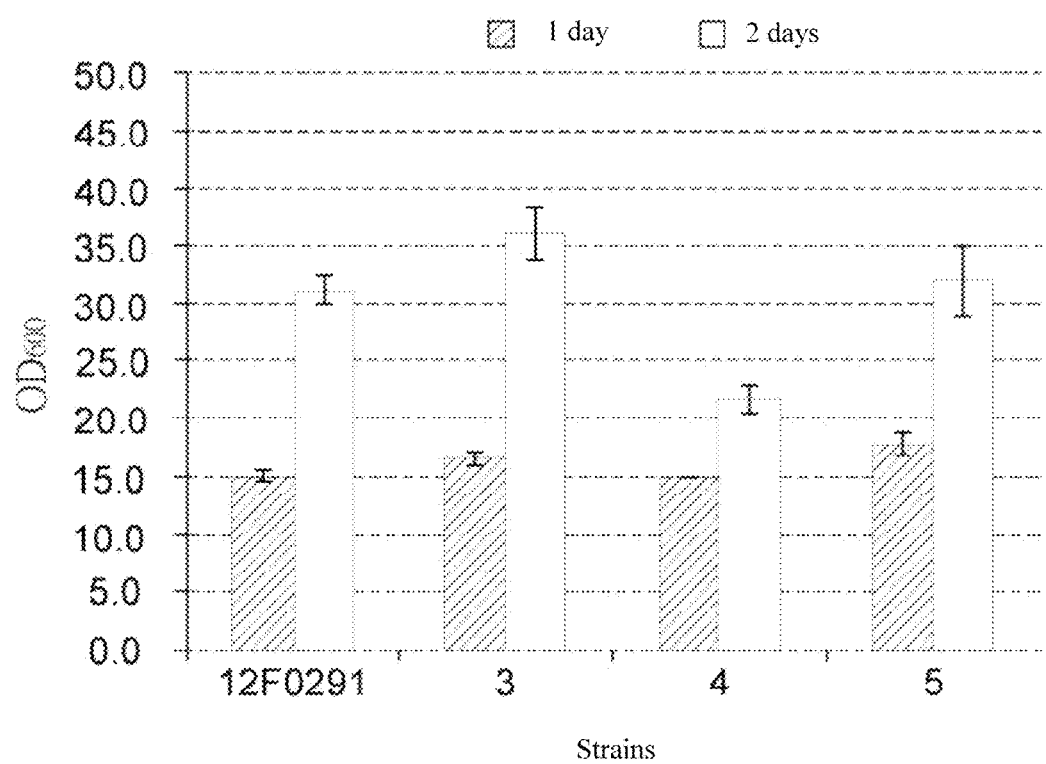
FIG. 10 illustrates cell numbers (represented in $OD_{600}$ value) of the *Aureobasidium pullulans* strains cultured in YM media for 1 or 2 days.
Figure 11:
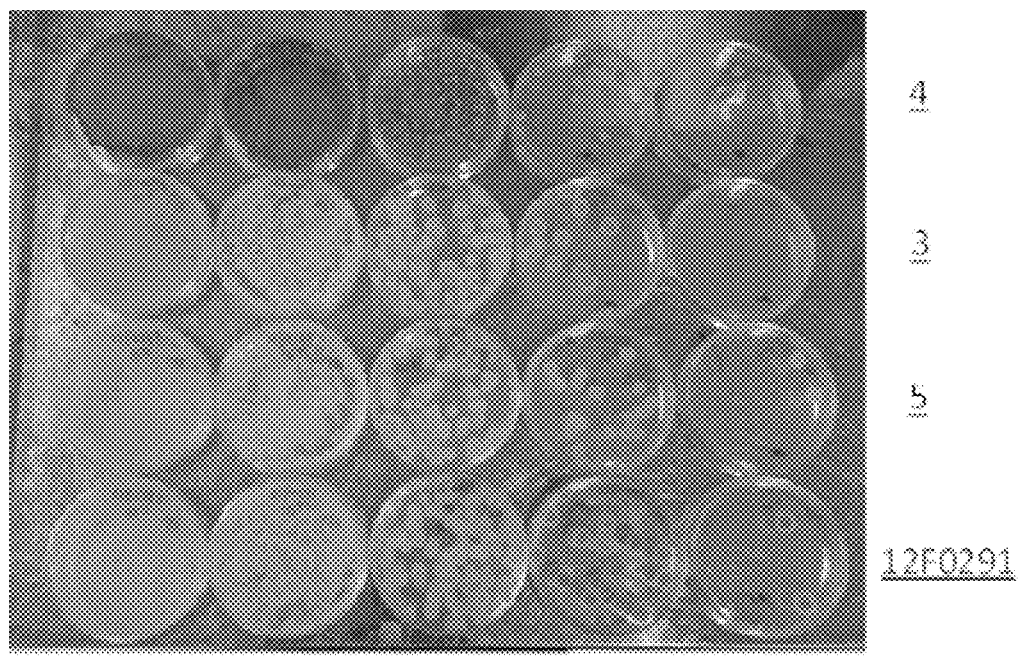
FIG. 11 illustrates colonies of the *Aureobasidium pullulans* cultured on YMA for 48 hours.

FIGS. 9 to 11 show an appearance of colonies, an appearance of shake flasks and colony numbers using plate count for *Aureobasidium pullulans* on YMA (top part of FIG. 9), or in YM culture media (middle part of FIG. 9) or fermentation culture media (bottom part of FIG. 9) after culture or fermentation. Wherein, the YMA comprises the ingredients listed in Table. 6 with additional agar of 15 g/L. As shown in FIG. 9, the broths of all four strains appeared beige in YM media, and the color of strain 4 was slightly deeper. However, in high-GCL fermentation culture media, the broth of strain 4 appeared slightly brown and the broth of strain 5 appeared slightly yellow, while that the broths of *Aureobasidium pullulans* 12F0291 and strain 3 appeared creamy white.

Results shown in FIG. 10 and Table 16 represent $OD_{600}$ values and viable cell counts for the inocula cultured for 24 and 48 hours, respectively. It can be understood that the four strains used in this embodiment showed similar growth rate, without obvious differences, after 24 hours of culture. However, after 48 hours of culture, an $OD_{600}$ value of strain 4 was apparently lower; that is, strain 4 showed a lower growth rate than strain 3. *Aureobasidium pullulans* 12F0291 and strain 5, on the other hand, showed similar growth rates.

TABLE 16

Viable cell counts of inocula after a 48-hour culture period

| Strain no. | Cell number (cfu/mL) | Cell number (LOG) |
|---|---|---|
| 12F0291 | $1.15 \times 10^8$ | 8.06 |
| 3 | $1.10 \times 10^8$ | 8.04 |
| 4 | $1.10 \times 10^8$ | 8.04 |
| 5 | $1.28 \times 10^8$ | 8.11 |

Figure 12:
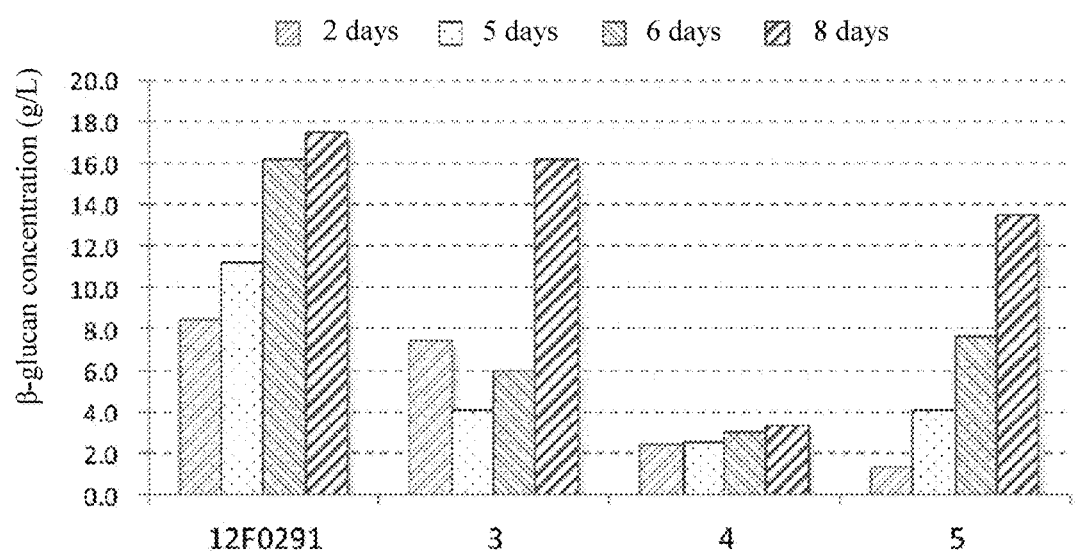
FIG. 12 illustrates concentrations of β-glucan in fermentation broths in which the *Aureobasidium pullulans* strains were fermented for 2, 5, 6 or 8 days.

Results shown in FIG. 12 were gathered from concentration measurements of β-glucan in fermentation broths after aforementioned strains were cultured for 2, 5, 6 and 8 days. It can be understood from FIG. 12 that β-glucan concentrations in fermentation broths of *Aureobasidium pullulans* 12F0291, strain 4 and strain 5 increased as the culture time increased. After 8 days of culture, the β-glucan concentration in the broth of strain 4 was about 3 g/L, lower than that in the broths of the other three strains. It should be noted that the concentration of β-glucan produced by strain 3 was 8 g/L after 2 days of culture, dropped to 4 g/L after 5 days of culture, and then increased significantly to 16 g/L after 8 days of culture. In sum, although the concentration of β-glucan produced by each strain varied, the method and the fermentation culture medium used according to this embodiment can surely enable the *Aureobasidium pullulans* strains to produce β-glucan.

In one embodiment, an *Aureobasidium pullulans* culture comprising β-glucan was provided, which was produced using the above method. It should be noted that an *Aureobasidium pullulans* culture produced with the above method may be further centrifuged or filtered to remove a fungus body thereof. In one embodiment, an *Aureobasidium pullulans* culture still comprising a fungus body may be applied to animal feeds, pet healthcare products, biocontrol agents, antagonistic yeast and so on. In another embodiment, an *Aureobasidium pullulans* culture of which a fungus body was removed may be applied to food, beverages, beauty drinks, cosmetics, care products and so on.

Therefore in another embodiment, a composition was provided, comprising the above *Aureobasidium pullulans* culture and an optional carrier. The composition may be used in, including but not limited to, fields of pharmaceuticals or food.

Given the composition of the present invention, a person of ordinary skill in the art may adopt known technologies to produce a dosage form suitable for parenteral or topical, or oral administration.

Preferably, the composition can be used to produce dosage forms suitable for oral administration, including but not limiting to: solution, suspension, emulsion, powder, tablet, pill, syrup, lozenge, troche, chewing gum, capsule, slurry and the likes.

The term "carrier" used herein may refer to a carrier which does not trigger allergic reactions or other undesirable effects inside the body of a subject during administration. In this application, the carrier may comprise one or more dosage forms selected from the following: solvent, emulsifier, suspending agent, decomposer, binding agent, excipient, stabilizing agent, chelating agent, diluents, gelling agent, preservative, lubricant or the likes.

Consequently, the above *Aureobasidium pullulans* culture or a composition comprising the culture may be used as food additives, and may be added using known techniques during ingredient preparation or prepared as food products for humans and non-humans.

According to the embodiments of the present invention, food products may include but not limit to: milk powder, beverages, confectionery, candies, fermented foods, animal feeds, health foods, dietary supplements, jellies, infant formulas, dressings, mayonnaise, spreads, creams, sauces, puddings, ice-cream, bakery products, ketchup, mustard, anti-staling agent, biocontrol agent (BCA) or antagonistic yeast.

In sum, an *Aureobasidium pullulans* according to an embodiment of the present invention is advantageous in producing no melanin (as shown in FIG. 9). Also, the yield of β-glucan can be effectively increased through improvements of the above culture media and culturing method.

Furthermore, with improvements in the manufacturing process and culture medium composition, all fermentation broth of the *Aureobasidium pullulans* can be used to manufacture β-glucan products with high concentrations of β-glucan, thereby making the products not only functional but also easy to store and further process. Liquid waste generated by the manufacturing process can also be reduced at the same time to achieve the goal of conserving energy and being environment-friendly. The manufacturing process as described above also keeps the functional substances in the *Aureobasidium pullulans* in addition to β-glucan.

The above descriptions are only illustrative and not to be taken in a limiting sense. It should be noted that any modifications and alterations made without departing from the spirit and scope of the invention shall be included in the protection scope of the appended claims.

What is claimed is:

1. A fermentation culture medium for producing β-glucan via *Aureobasidium pullulans*, comprising:
  a carbon source, a lecithin and an ascorbic acid,
  wherein the carbon source is selected from a group consisting of: lactose, fructose, maltose, glucose, galactose, xylose, xylitol, inulin, sorbitol, fucose, sucrose, molasses and a combination thereof, wherein the *Aureobasidium pullulans* is deposited at National Institute of Technology and Evaluation (NITE), NITE Patent Microorganisms Depositary (NPMD) on Oct. 19, 2016 under the accession number NITE BP-02372.

2. The fermentation culture medium according to claim 1, wherein the carbon source is sucrose or glucose.

3. The fermentation culture medium according to claim 2, wherein a concentration of the sucrose is 10-70 g/L based on a total volume of the culture medium.

4. The fermentation culture medium according to claim 2, wherein a concentration of the glucose is 25-150 g/L based on a total volume of the culture medium.

5. The fermentation culture medium according to claim 1, wherein a concentration of the lecithin is lower than or equals to 6 g/L based on a total volume of the culture medium.

6. The fermentation culture medium according to claim 1, wherein a concentration of the ascorbic acid is lower than or equals to 6 g/L based on a total volume of the culture medium.

7. The fermentation culture medium according to claim 1, wherein an initial pH value of the fermentation culture medium is 4-8.

8. The fermentation culture medium according to claim 7, wherein an initial pH value of the fermentation culture medium is 5-6.

9. A method for producing β-glucan, comprising: culturing an *Aureobasidium pullulans* in a fermentation culture medium for fermentation, wherein the fermentation culture medium comprises a carbon source, a lecithin and an ascorbic acid; and wherein the carbon source is selected from a group consisting of: lactose, fructose, maltose, glucose, galactose, xylose, xylitol, inulin, sorbitol, fucose, sucrose, molasses and a combination thereof, wherein the *Aureobasidium pullulans* is deposited at National Institute of Technology and Evaluation (NITE), NITE Patent Microorganisms Depositary (NPMD) on Oct. 19, 2016 under the accession number NITE BP-02372.

10. The method according to claim 9, wherein the *Aureobasidium pullulans* is cultured at 15-30° C.

11. The method according to claim 9, wherein the fermentation is carried out with a rotation speed of 150-350 rpm.

12. The method according to claim 9, wherein the fermentation is carried out with a ventilation of 1-2 vvm.

13. The method according to claim 9, further comprising culturing the *Aureobasidium pullulans* in an inoculum culture medium to enable the *Aureobasidium pullulans* to proliferate until a stationary phase before fermentation.

14. The method according to claim 9, wherein the inoculum culture medium comprises yeast extract granulated, malt extract, peptone from soybean (enzymatic digest), dextrose and $H_2O$.

15. An *Aureobasidium pullulans* culture comprising β-glucan, which is produced by the method according to the claim 9.

16. A composition, comprising the *Aureobasidium pullulans* culture of claim 15, and an optional carrier.

* * * * *